US011694412B2

(12) United States Patent
Settlemier et al.

(10) Patent No.: US 11,694,412 B2
(45) Date of Patent: Jul. 4, 2023

(54) ULTRASONIC CARDIAC ASSESSMENT OF HEARTS WITH MEDIAL AXIS CURVATURE AND TRANSVERSE ECCENTRICITY (71) Applicant: KONINKLIJKE PHILIPS N.V., Eindhoven (NL)

(72) Inventors: Scott Holland Settlemier, Marlborough, MA (US); David Prater, Andover, MA (US); Robert Joseph Schneider, Windham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 702 days.

(21) Appl. No.: 15/776,820

(22) PCT Filed: Nov. 23, 2016

(86) PCT No.: PCT/IB2016/057052
§ 371 (c)(1),
(2) Date: May 17, 2018

(87) PCT Pub. No.: WO2017/093852
PCT Pub. Date: Jun. 8, 2017

(65) Prior Publication Data
US 2018/0357832 A1 Dec. 13, 2018

Related U.S. Application Data (60) Provisional application No. 62/261,906, filed on Dec. 2, 2015.

(51) Int. Cl.
*A61B 8/08* (2006.01)
*G06T 19/20* (2011.01)
(Continued)

(52) U.S. Cl.
CPC ............ *G06T 19/20* (2013.01); *A61B 8/0883* (2013.01); *A61B 8/463* (2013.01); *A61B 8/466* (2013.01);
(Continued)

(58) Field of Classification Search
CPC .......... G06T 19/20; G06T 7/12; G06T 7/149; G06T 13/20; G06T 19/00;
(Continued)

(56) References Cited

U.S. PATENT DOCUMENTS 5,474,073 A 12/1995 Schwart et al.
5,485,842 A 1/1996 Quistgaard
(Continued)

FOREIGN PATENT DOCUMENTS

EP 2397076 A1 12/2011
JP 2006314790 A 11/2006
(Continued)

OTHER PUBLICATIONS

Crum W R, Non-rigid image registration: theory and practice, 2004, The British Journal of Radiology (Year: 2004).*
(Continued)

*Primary Examiner* — Katherine L Fernandez
*Assistant Examiner* — Brooke Lyn Klein (57) ABSTRACT An ultrasonic imaging system produces more diagnostic cardiac images of the left ventricle by plotting the longitudinal medial axis of the chamber between the apex and mitral valve plane as a curved line evenly spaced between the opposite walls of the myocardium. Transverse image planes are positioned orthogonal to the curved medial axis with control points positioned in the short axis view on lines evenly spaced around and emanating from the medial axis. If the short axis view is of an oval shaped chamber the transverse image is stretched to give the heart a more rounded appearance resulting in better positioning of editing control points.

14 Claims, 8 Drawing Sheets (51) Int. Cl.
  *A61B 8/00* (2006.01)
  *G06T 19/00* (2011.01)
  *G06T 7/149* (2017.01)
  *G06T 7/12* (2017.01)
  *G06T 13/20* (2011.01)

(52) U.S. Cl.
  CPC .............. *A61B 8/467* (2013.01); *A61B 8/483* (2013.01); *A61B 8/52* (2013.01); *A61B 8/523* (2013.01); *A61B 8/5253* (2013.01); *A61B 8/5269* (2013.01); *G06T 7/12* (2017.01); *G06T 7/149* (2017.01); *G06T 13/20* (2013.01); *G06T 19/00* (2013.01); *G06T 2207/10136* (2013.01); *G06T 2207/20096* (2013.01); *G06T 2207/30048* (2013.01); *G06T 2207/30172* (2013.01); *G06T 2210/41* (2013.01); *G06T 2219/008* (2013.01); *G06T 2219/2021* (2013.01)

(58) Field of Classification Search
  CPC . G06T 2207/10136; G06T 2207/20096; G06T 2207/30048; G06T 2207/30172; G06T 2210/41; G06T 2219/008; G06T 2219/2021; A61B 8/0883; A61B 8/463; A61B 8/466; A61B 8/467; A61B 8/483; A61B 8/52; A61B 8/5253; A61B 8/5269
  See application file for complete search history.

(56) References Cited

U.S. PATENT DOCUMENTS

| | | | |
|---|---|---|---|
| 5,720,291 A | 2/1998 | Schwartz | |
| 5,883,613 A | 3/1999 | Iwaki | |
| 6,013,032 A | 1/2000 | Savord | |
| 6,186,950 B1 | 2/2001 | Averkiou et al. | |
| 6,375,617 B1 | 4/2002 | Fraser | |
| 6,443,896 B1 | 9/2002 | Detmer | |
| 6,491,636 B2 * | 12/2002 | Chenal | A61B 6/463 600/450 |
| 6,692,438 B2 | 2/2004 | Skyba et al. | |
| 7,010,164 B2 | 3/2006 | Weese et al. | |
| 7,167,172 B2 | 1/2007 | Kaus et al. | |
| 7,421,122 B2 | 9/2008 | Kaus et al. | |
| 7,565,000 B2 | 7/2009 | Capolunghi et al. | |
| 7,853,304 B2 | 12/2010 | Baumann et al. | |
| 9,019,272 B2 | 4/2015 | Nijunsing | |
| 2002/0072672 A1 | 6/2002 | Roundhill et al. | |
| 2005/0075567 A1 | 4/2005 | Skyba et al. | |
| 2006/0291705 A1 * | 12/2006 | Baumann | G06T 15/08 382/128 |
| 2009/0028404 A1 * | 1/2009 | Bussadori | A61B 8/488 382/130 |
| 2010/0189317 A1 | 7/2010 | Lehmann et al. | |
| 2011/0098562 A1 * | 4/2011 | Saigo | G01S 7/52042 600/437 |
| 2015/0317789 A1 * | 11/2015 | Codella | G06K 9/468 382/133 |

FOREIGN PATENT DOCUMENTS

| | | |
|---|---|---|
| JP | 2012029722 A | 2/2012 |
| WO | 2005054898 A1 | 6/2005 |
| WO | 2006024970 A1 | 3/2006 |
| WO | 2011121493 A1 | 10/2011 |
| WO | 2014024758 A1 | 2/2014 |

OTHER PUBLICATIONS

Miriam S et al., "Mitral valve morphology assessment: Three dimensional transesophageal echocardiography versus computed tomography", The society of thoracic surgeons, 2010.

* cited by examiner

ULTRASONIC CARDIAC ASSESSMENT OF HEARTS WITH MEDIAL AXIS CURVATURE AND TRANSVERSE ECCENTRICITY

This application is the U.S. National Phase application under 35 U.S.C. § 371 of International Application No. PCT/IB2016/057052, filed on Nov. 23, 2016, which claims the benefit of Provisional Application Ser. No. 62/261,906, filed Dec. 2, 2015. These applications are hereby incorporated by reference herein.

This invention relates to medical diagnostic ultrasound systems and, in particular, to ultrasound systems which perform cardiac assessment of hearts with axial curvature and transverse irregularity.

Ultrasonic imaging is widely used to assess and diagnose the condition of the heart. An ultrasound probe pressed against the body of a patient just below the rib cage and aimed upward to view the heart from its apex. When the heart is fully in view in real time images, a sequence of three dimensional image datasets is acquired over a heart cycle. The three dimensional image data is analyzed by a segmentation processor to identify various features and characteristics of the heart, such as the endothelial border of the left ventricle, ejection fraction, and myocardial motion. Two such processors for cardiac analysis are the automated border detection processor described in U.S. Pat. No. 6,491,636 (Chenal et al.) and the heart model processor described in U.S. Pat. No. 7,101,164 (Weese et al. and US Pat. pub. no. 2010/0189317 (Lehmann et al.) With analytical tools such as these, the clinician can command the processor to segment the cardiac data over the heart cycle, identifying the valves and chambers of the heart and showing the heart in standard ASE views from which diagnosis proceeds. However, since there is a great variability among patients as to patient size, body habitus, and heart shapes and orientation, the clinician will edit the automatically delineated borders to best fit the anatomical boundaries that the clinician perceives in the images. Two characteristics which pose problems for this editing are a pronounced longitudinal curvature and/or an eccentric transverse shape of the heart. A longitudinal curvature of the left ventricle can preclude an MPR (multiplanar reconstructed) image plane through the three dimensional image data from being able to show an adequate long axis presentation in all of the standard ASE views. Transverse eccentricity of the heart can make border delineation more difficult and edit control spacing less regular. Accordingly it is desirable for an ultrasonic cardiac diagnostic processor to adequately present a long axis view of the heart, with good border orthogonality and edit control spacing in each of the standard ASE views.

In some aspects, the present invention includes ultrasound systems and methods. For example, the present invention can include an ultrasonic diagnostic imaging system for cardiac diagnosis. The system can have instruction thereon, which when executed cause the system to: acquire, using a probe, three dimensional ultrasound image datasets of including the a heart, produce image data of a myocardium and a heart chamber, delineate a curved medial axis of the heart chamber between a longitudinally separated apex and valve plane which that is substantially evenly positioned between opposite walls of the myocardium, and display a heart chamber image in a plane of the curved medial axis.

In certain aspects, the systems of the present invention can include an ultrasonic diagnostic imaging system for cardiac diagnosis that includes a probe configured to acquire three dimensional ultrasound image datasets including a heart, a first processor configured to produce image data of a myocardium and a heart chamber, a second processor configured to delineate a curved medial axis of the heart chamber between a longitudinally separated apex and valve plane that is substantially evenly positioned between opposite walls of the myocardium, and a display for displaying a heart chamber image in a plane of the curved medial axis.

In some aspects, the present invention includes a method of diagnosing a patient by ultrasonic cardiac imaging. The method can include acquiring a sequence of three dimensional image datasets of a heart, extracting a long axis view of a myocardium and heart chamber, and delineating a curved medial axis of the heart chamber between an apex and valve plane which is evenly spaced between opposite walls of the myocardium.

In accordance with the principles of the present invention, an ultrasonic diagnostic system and method are described which correct for heart curvature and transverse eccentricity in ultrasonic cardiac images. The usual straight-line medial axis is plotted as a curved line evenly spaced between the chamber walls and extending from the apex to mitral valve plane. Transverse eccentricity is reduced by stretching the myocardium in the image to produce a more uniform shape. As a result of these measures, the borders of the cardiac chamber are presented such that chamber walls are more equidistant and orthogonal to the viewing plane, enabling the creation of more complete long axis MPR views and allowing for in-plane edits of transverse MPR planes to represent more equidistant and orthogonal displacement of segmented boundaries and control points. Non-foreshortened long axis MPR views are produced which are curvilinear slices that pass through the curved medial axis. Editing of the control points in one of the standard views will now operate more independently of the other views and improve the visualization and diagnosis of the interface being delineated.

Figure 1:
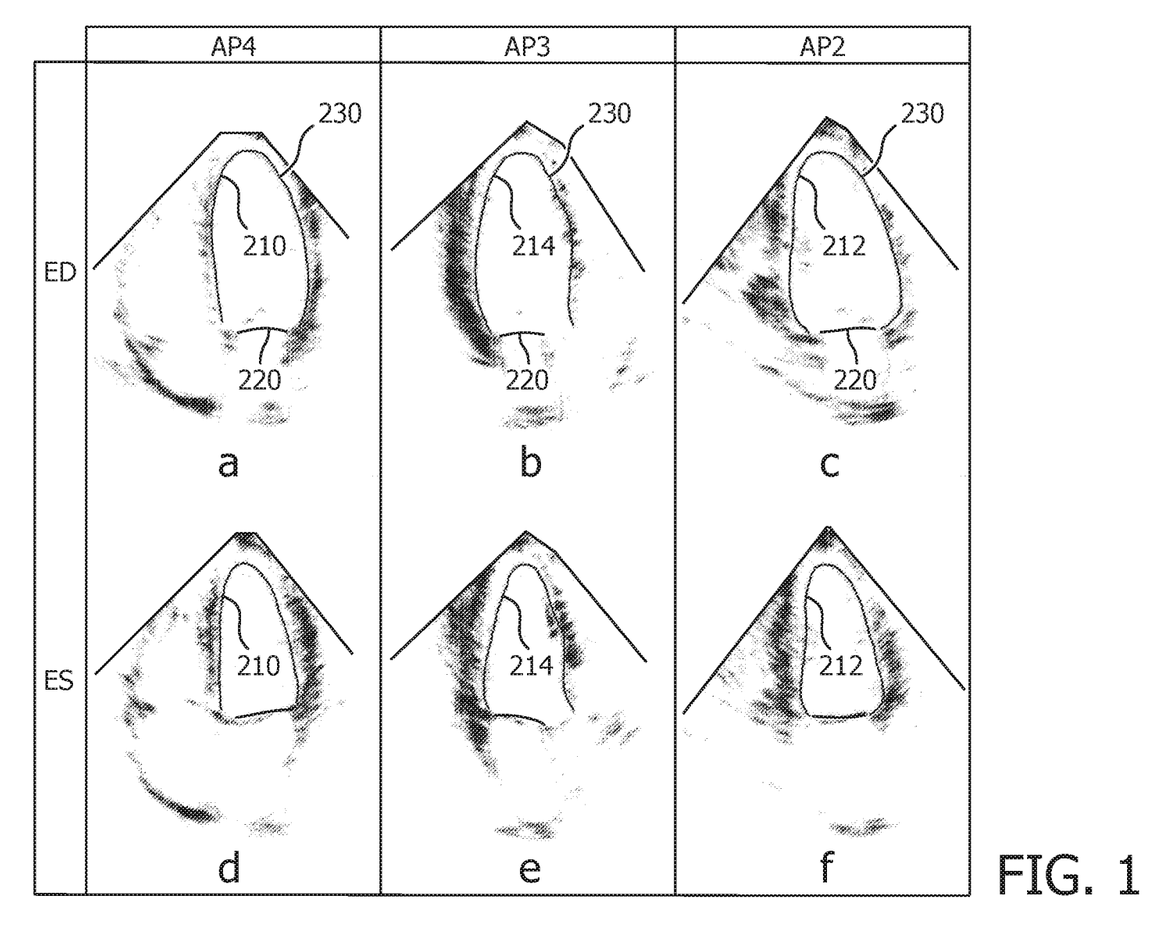
FIG. 1 illustrates standard ASE views of a heart at end diastole and end systole.

FIG. 1 illustrates three standard views of a heart from which diagnosis proceeds, and apical four-chamber (AP4) view, an apical three-chamber (AP3) view, and an apical two-chamber (AP2) view. The top three images a, b, and c are of a heart at the end diastole phase, and the bottom three images d, e, and f are of the heart at the end systole phase. Image analysis tools such as the Heart Model, part of the QLAB feature on Philips Healthcare (Andover, Mass.) ultrasound systems, can automatically segment these standard view planes as MPR image planes from volume (3D) data of a heart. The QLAB feature is also capable of automatically tracing borders of the heart in an ultrasound cardiac image, such as the boundary 210, 212 and 214 of the left ventricle (LV) and the mitral valve plane 220 in these views as illustrated in FIG. 1. Similarly, borders can be automatically traced for other features of the heart, such as the right ventricle.

Figure 2A:
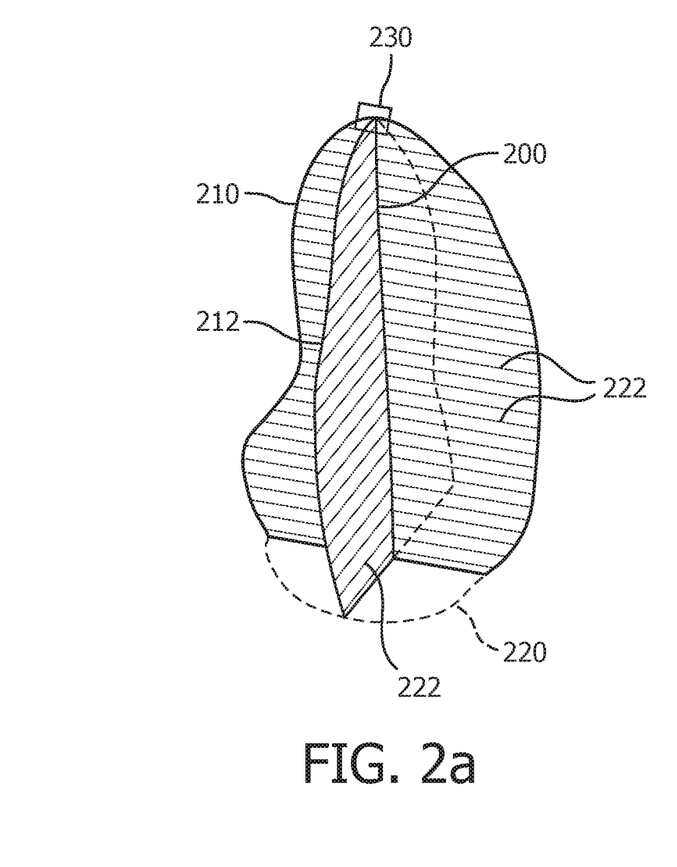
FIG. 2a illustrates the intersection of the planes of the left ventricular chamber in two standard views.
Figure 2B:
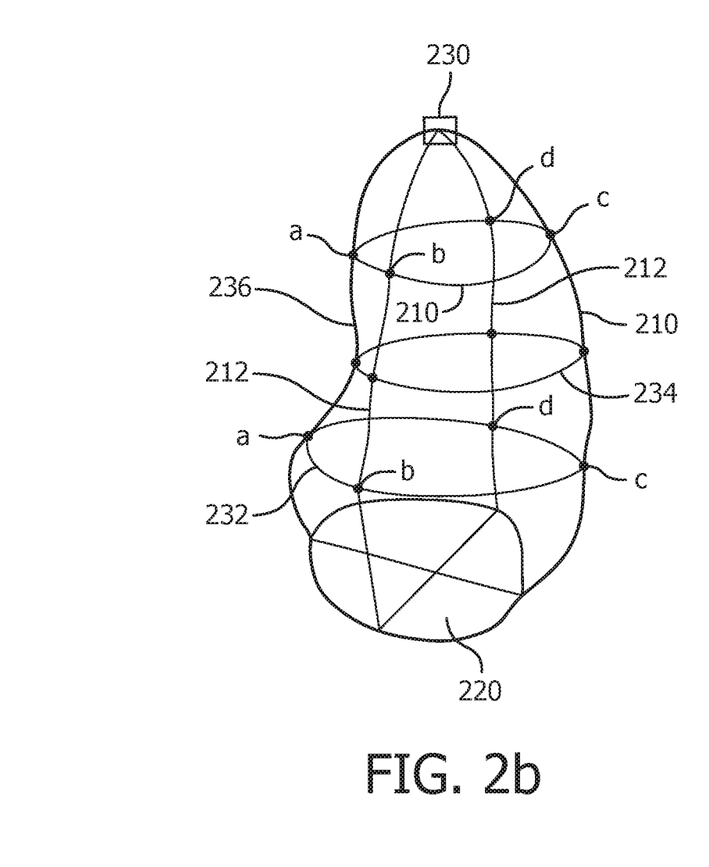
FIG. 2b a three dimensional mesh of the left ventricle with control points for editing.

The three standard view planes intersect each other at a common medial axis of the LV at relative rotational angles of approximately 0°, 60° and 100°. The intersection of two of the standard view planes is illustrated in FIG. 2a, where the LV plane in the AP4 view, outlined at 210, is shown intersecting the LV plane of the AP2 view, outlined at 212, at medial axis 200. Also shown in FIG. 2a are lines 222 indicating where transverse (short axis) view planes may be reconstructed as MPR images from the volume image data. Since all these two dimensional view planes are extracted from the same volume image data, their heart wall outlines can be organized as a mesh or wire frame model of the three dimensional left ventricular chamber as shown in FIG. 2b. The points where the different border tracings intersect each other are marked as a, b, c in the drawing. While the FIG. 2a drawings represent an ideal case, in practice the 3D image data may not be fully susceptible to identifying the entirety of all of the border tracings 210, 212, 232, 234 and 236 (and others) automatically, or at least not to the complete satisfaction of the diagnosing physician. Thus, the QLAB image diagnosis program creates control points around automatically drawn borders which can be manipulated by the physician to relocate the border tracing relative to the image. When the physician pulls or moves a control point in a view plane with a pointing device such as a trackball or mouse, the border tracing will move to a new position with the control point but remain smoothly connected to adjacent control points, a process known as "rubberbanding." In FIG. 2b intersection points a, b, and c can be used as control points for the illustrated border tracings. A problem arises, however, if the control points are located too close to each other. In such case, the border processing program cannot smoothly reposition the connected border tracing. Instead, the tracing will jump and become unstable as the physician attempt movement of a control point. Furthermore, attempts to reposition a control point in one view plane can affect the position of a tracing and control point in another view plane when the control points are too close together. As FIG. 2b illustrates, the borders of the different view planes are all spatially interrelated by their relation to the common 3D image dataset. Hence it is desirable to have regular, even spacing of the control points so that editing of their position will not cause instability of the tracing or affect the border tracings and control points in other view planes.

Figure 3A:
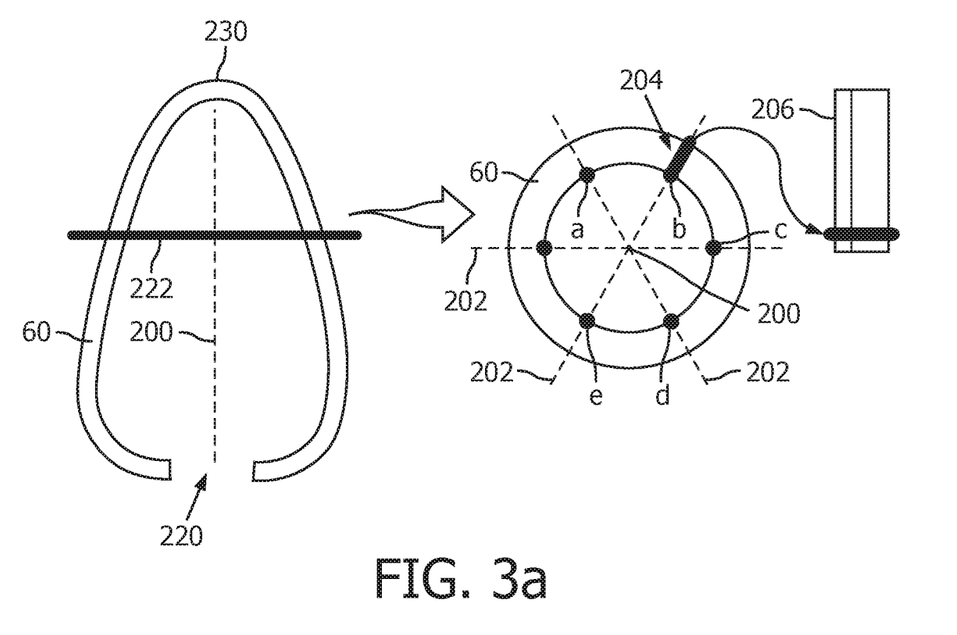
FIG. 3a illustrates the medial axis and control points of longitudinal and transverse cardiac images for a uniformly symmetrical heart shape.

With images of a longitudinally straight and uniformly symmetrical heart these editing problems generally do not arise. FIG. 3a illustrates the myocardium 60 of a longitudinally straight and symmetrical heart. Its medial axis 200, automatically drawn between the apex 230 of the heart and the center of the mitral valve plane 220 at the bottom of the LV, is straight down the center of the LV chamber. A flat view plane that passes through the straight medial axis 200 will capture a complete, non-foreshortened long axis view of the LV. When a transverse view plane 222 is created orthogonal to the medial axis 200, the symmetrical myocardium 60 will appear approximately circular, as shown on the right side of FIG. 3a. When evenly angularly distributed control point positioning lines 202 are located emanating from the medial axis 200, their intersection with the heart wall produce evenly distributed control points a, b, c, d, and e. Furthermore the positioning lines are seen to intersect the myocardium orthogonally. This produces the short path 204 through the endocardial border and myocardium, useful for measuring correct myocardial thickness, as illustrated by bar 206.

Figure 3B:
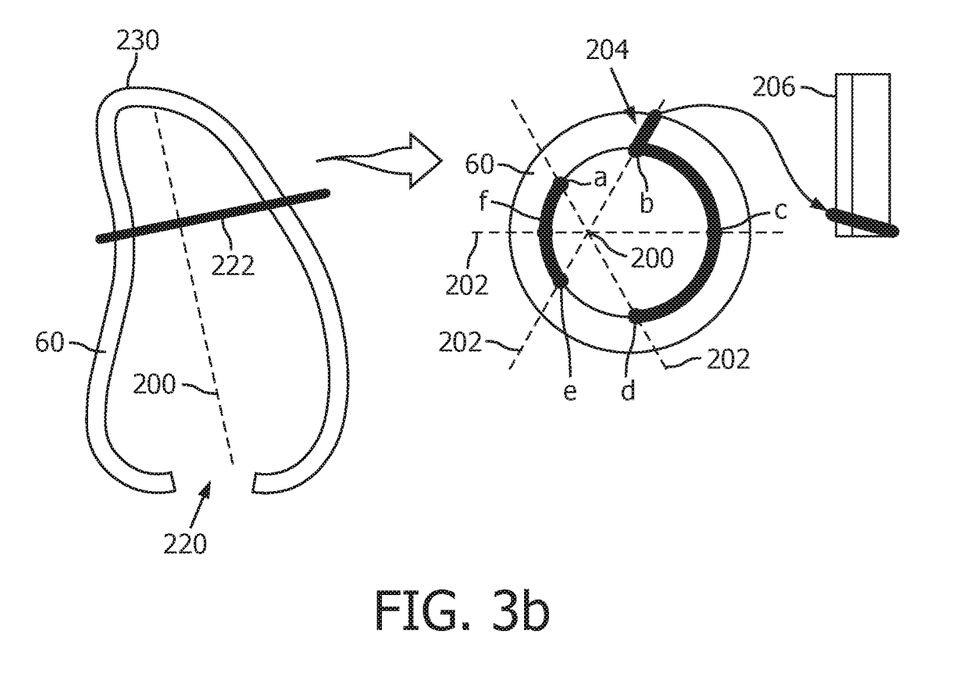
FIG. 3b illustrates the medial axis and control points of longitudinal and transverse cardiac images for a heart with a longitudinally curved shape.

Not all hearts are ideally shaped for this image analysis, however. FIG. 3b illustrates the myocardium 60 of a heart with a curved longitudinal shape, a so-called banana-shaped heart. When the medial axis 200 is drawn between the apex 230 and the mitral valve plane 220, it is seen to be closer to the left side of the heart and further from the right side of the heart as the drawing illustrates. An orthogonally located transverse plane 222 will appear as shown to the right in the drawing, with the medial axis 200 close to the left side of the heart and far from the right side. When the control point positioning lines 202 are drawn emanating from the medial axis 200 their points of intersection with the myocardium 60 are not uniformly distributed around the heart. Control points b, c, and d are widely separated, and points a, f and e are much closer together. When the physician attempts to reposition control point f, it can cause instability and inadvertent repositioning of closely adjacent points a and e. Furthermore, the positioning lines 202 do not intersect the heart wall orthogonally, but at different angles. Measurement of the endocardial border and myocardial thickness are distorted and inaccurate, as illustrated by the tilted positioning line through the bar 206 to the right in the drawing.

Figure 3C:
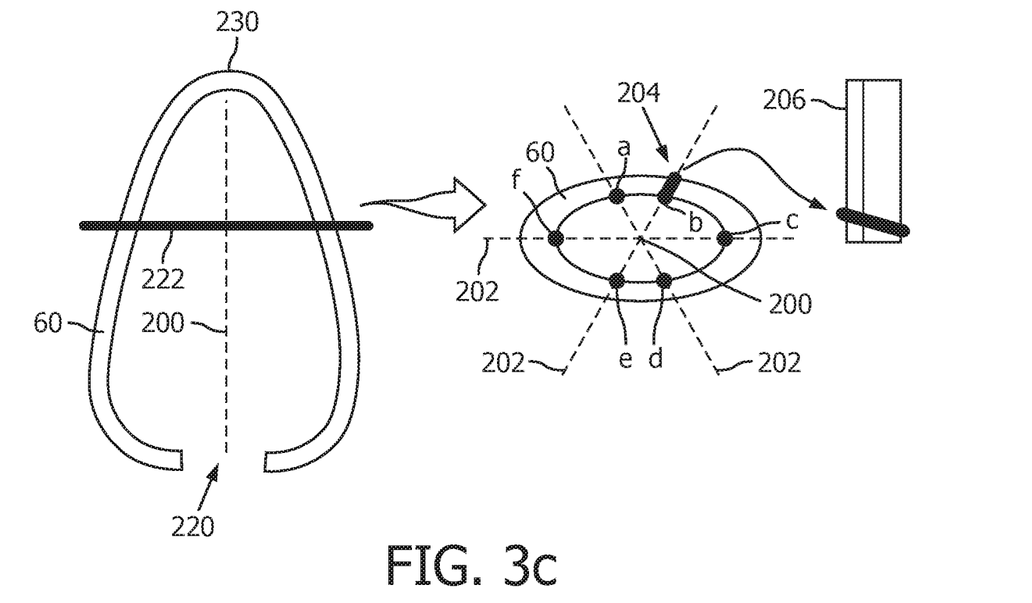
FIG. 3c illustrates the medial axis and control points of longitudinal and transverse cardiac images for a heart with an eccentric transverse shape.

FIG. 3c illustrates a condition where the myocardium is not longitudinally curved, but is more transversely oval rather than rounded as shown to the right in the drawing. The oval shape of the myocardium causes the control points a, b and d, e to be too closely spaced and control points c and f to be widely separated from their adjacent control points. While the horizontal control point positioning line intersects the myocardium 60 orthogonally in the short axis view, the intersections of the other positioning lines 202 are not orthogonal, again causing a distortion of the thickness of the myocardium along the positioning lines, as shown at 204 and in bar 206.

Figure 3D:
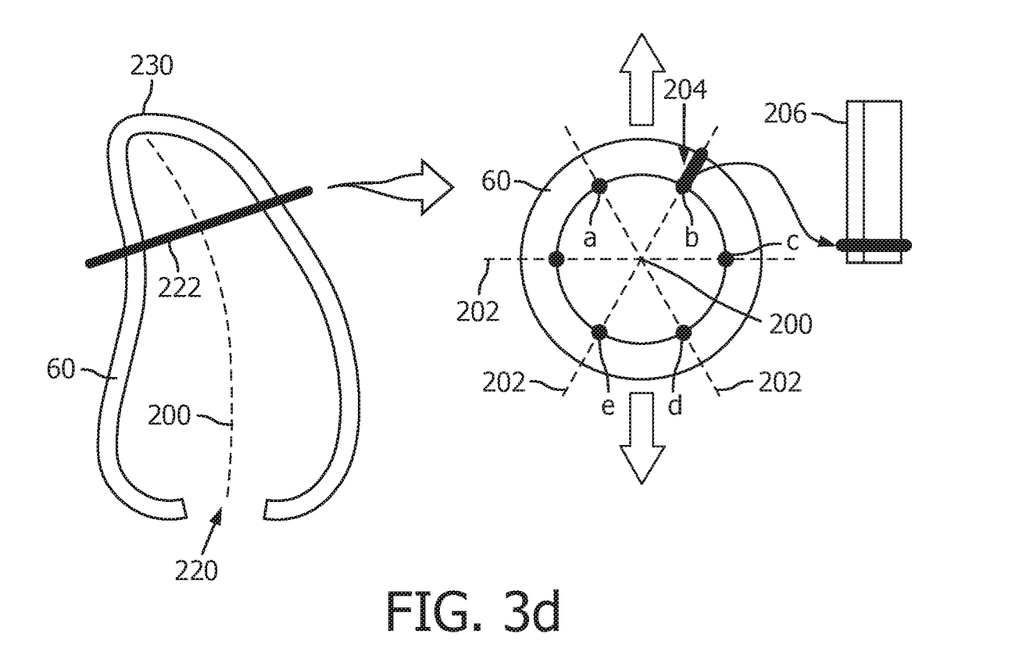
FIG. 3d illustrates the medial axis and control points of longitudinal and transverse cardiac images of a heart corrected for these irregularities in accordance with the principles of the present invention.

In accordance with the principles of the present invention, these problems are mitigated by plotting a curved medial axis 200 as shown in FIG. 3d. The medial axis 200 is drawn, not as a straight line between the apex 230 and the mitral valve plane 220, but as a curve which is evenly positioned between the opposite sides of the heart in the view plane as shown in FIG. 3d. The curve may not rigorously follow the heart anatomy, but may be smoothed by the image processing software into a smooth curve, rather than a jagged and rapidly changing curve. A quadratic curve model is preferred for such smoothly curved axes. The result is illustrated by the smooth medial axis curve 200 on the left side of FIG. 3d. Compared with FIG. 3b, the curved medial axis causes orthogonal transverse axis image planes to have a more centrally located medial axis 200 from which evenly spaced control point positioning lines 202 will intersect the myocardium in the short axis more orthogonally, as shown on the right side of FIG. 3d. This will create a more orthogonal path the myocardium as shown at 204 and by bar 206, accurately indicating the true myocardial thickness. In accordance with a further aspect of the present invention, any pronounced oval shaping of the myocardium in the short axis view is reduced by "stretching" the myocardium in the image with the image processing software to produce a more rounded shape, as indicated by the arrows on the right side of FIG. 3d. Centerline-orthogonal affine stretching is preferred for this image processing. When both of these modifications are applied, the transverse view of the heart and its cut planes appear more like those of the ideal heart shape of FIG. 3a, and will enable heart measurements which are closer to those which a diagnosing physician is seeking.

Figure 4:
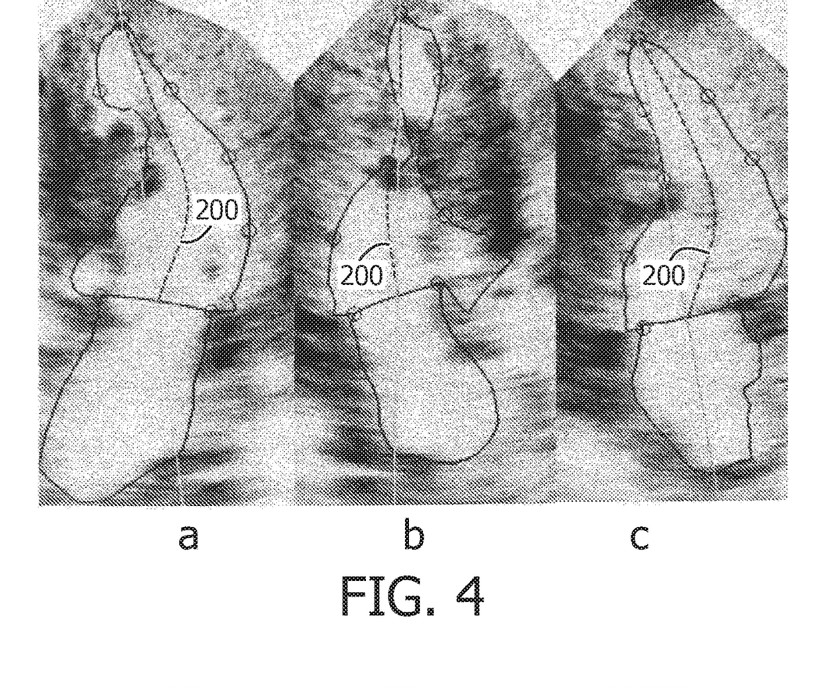
FIG. 4 shows three cardiac images of hearts with longitudinal curvature.

Since the viewing medium for an ultrasound system is a flat display, the benefit of the medial axis curvature for a long axis view is best presented to the diagnosing physician by sampling the 3D image data to produce a curvilinear slice that passes through the curved medial axis, then straightening the curved image to a flat plane for display. The final image will thus show the medial axis, when displayed, as a straight line. The results of elastic deformation of the curved plane intersecting the curved medial axis may be appreciated by viewing the images of FIGS. 4 and 5. In FIG. 4, the medial axis 200 in anatomically correct images of the LV has been curved as discussed above in heart images a, b, and c. When elastic deformation is performed to view the curved planes defined by the curved medial axes 200 as flat planes in the plane of the ultrasound system image display, the LV appears as shown in FIGS. 5a, b, and c, respectively, with the medial axes shown as straight lines. As the images illustrate, the boundary and area of the LV in the processed images of FIG. 5 are less irregular and lend themselves more readily to diagnosis and measurement.

Figure 5:
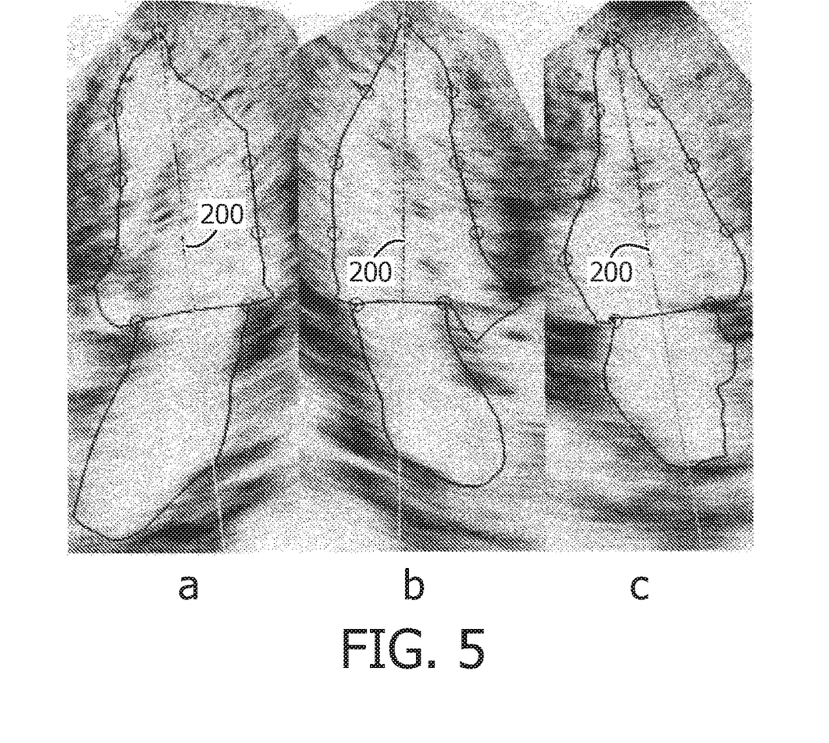
FIG. 5 shows the same heart data after correction with curved MPRs in accordance with the principles of the present invention.
Figure 6:
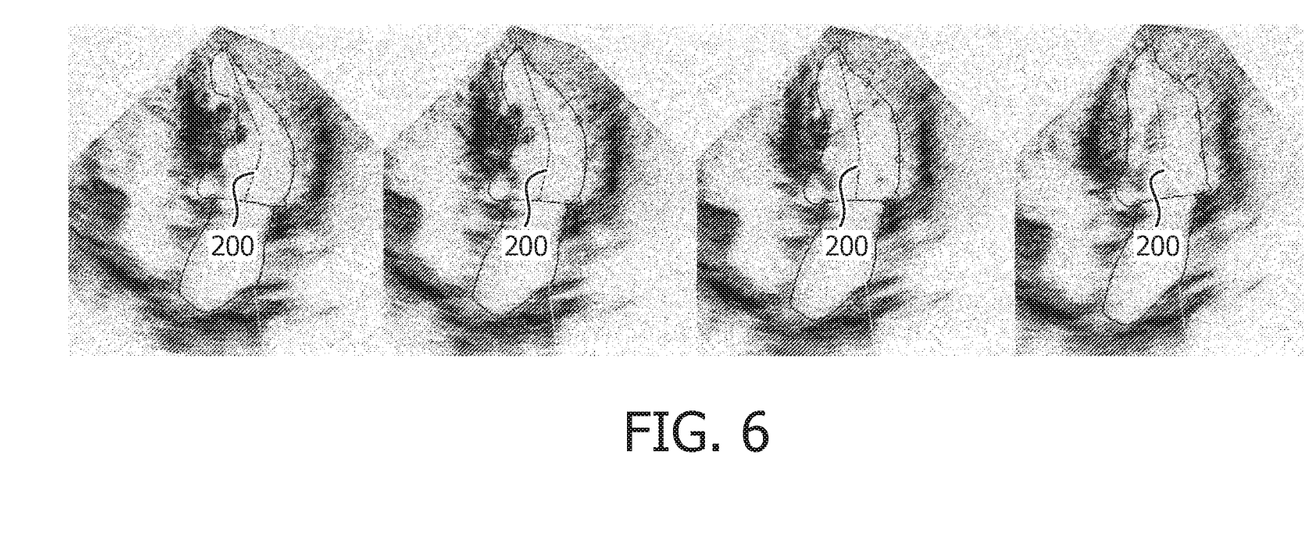
FIG. 6 illustrates animation of the transition from planar to curved MPRs of a heart in accordance with the present invention.

It is important that the diagnosing physician recognize that the processed images of FIG. 5 are not the anatomically correct images acquired by the ultrasound system, but have been processed to be more susceptible to diagnosis and measurement. In accordance with a further aspect of the present invention, an ultrasound system of the present invention can produce an animation of the change from an image with a curved medial axis image to one in which the curvature has been straightened, as illustrated in FIG. 6. The image on the left side of FIG. 6 is the image of FIG. 4a, in which the medial axis has been drawn as a curved line positioned evenly between the opposite side walls of the anatomically correct LV. The image on the right side of FIG. 6 is that of FIG. 5a, which results from deformation of the curved axis MPR plane to a straight one. The intermediate images between the left and right ends of FIG. 6 illustrate two images produced in a sequence of progressive straightening of the medial axis. When these images (and others) are played to the diagnosing physician by the image processing software as an animation sequence, the physician can readily grasp the image processing effect on the original image on the left, and observe how it has been changed to the more diagnostic but less anatomically correct image on the right.

Figure 7A:
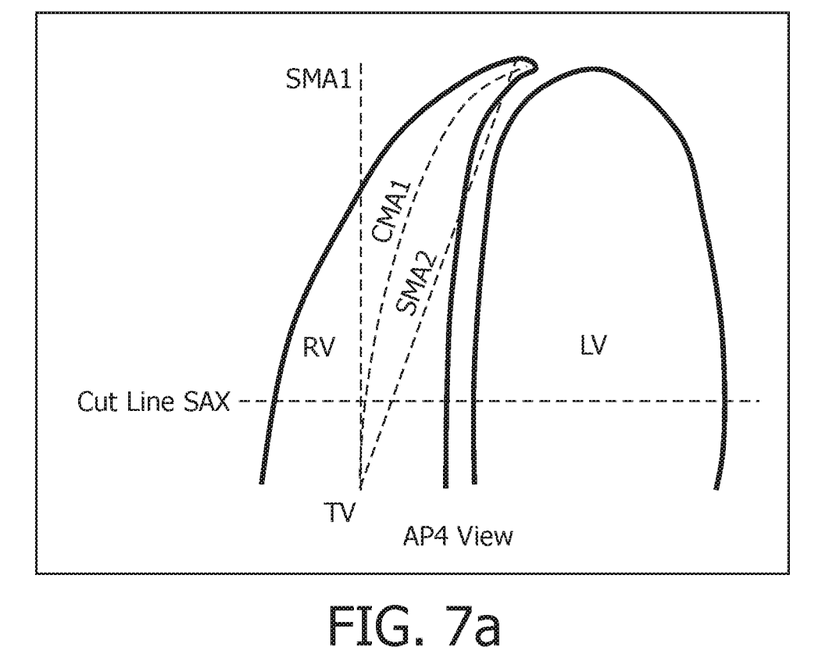
FIG. 7 illustrates the intersection of MPR planes of a right ventricular chamber in two standard views.
Figure 7B:
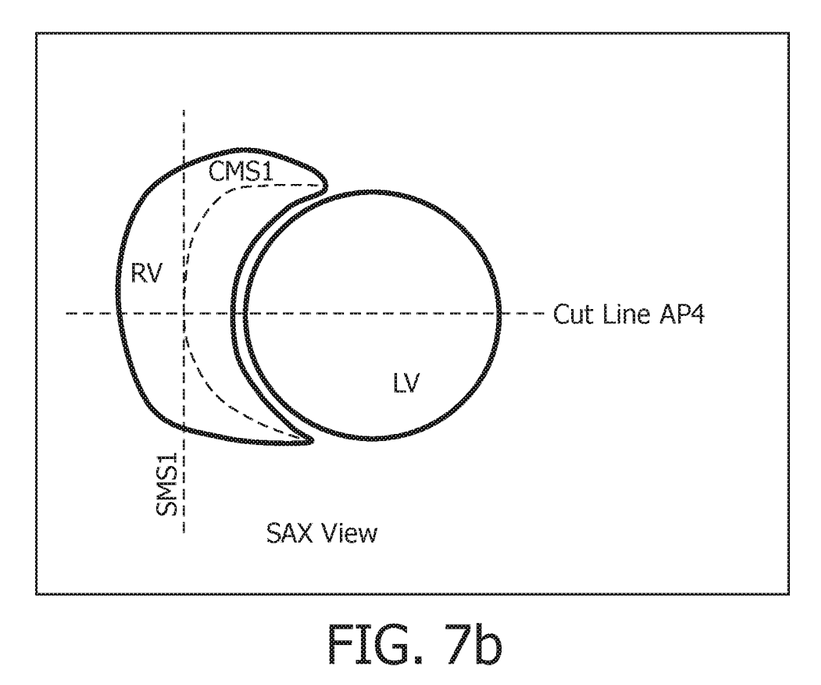

As explained for the left ventricle, the present disclosure can be used for other heart chambers, such as the right ventricle (RV), as well. FIGS. 7A and 7B show examples of using a curved MPR plane for a curved right ventricle. The AP4 view in FIG. 7A shows three MPR planes as identified by the dashed lines, referred to as a straight MPR Apical 1 (SMA1), a straight MPR Apical 2 (SMA2), and curved MPR apical (CMA1). The SMA1 is positioned at the center of the tricuspid valve (TV), and further orthogonal to the AP4 view plane and the short-axis view plane (SAX). Here, SMA1 results in a foreshortened view of the RV chamber. Alternatively, SMA2 can be oriented to pass through the TV and the apex of the RV, but this view also results in a foreshortened or inaccurate view of the RV chamber. As shown, the CMA1 plane, which is determined similar to the LV analysis described above, is positioned evenly between walls of the right ventricle and contains both the tricuspid valve and the apex of the RV. FIG. 7B shows a short axis view of the right ventricle in FIG. 7A, along with the cut line for the AP4 view. Similar to the problems with SMA1 and SMA2, an MPR plane identified as a straight MPR short-axis 1 (SMS1) is positioned at the center of the right ventricle, but it does not fully slice through the crescent-shaped RV. In contrast, the curved MPR plane, curved MPR short-axis 1 (CMS1), is positioned at the medial axis of the RV as seen in the short-axis view, and it spans from each tip of the crescent-shaped RV.

Figure 8:
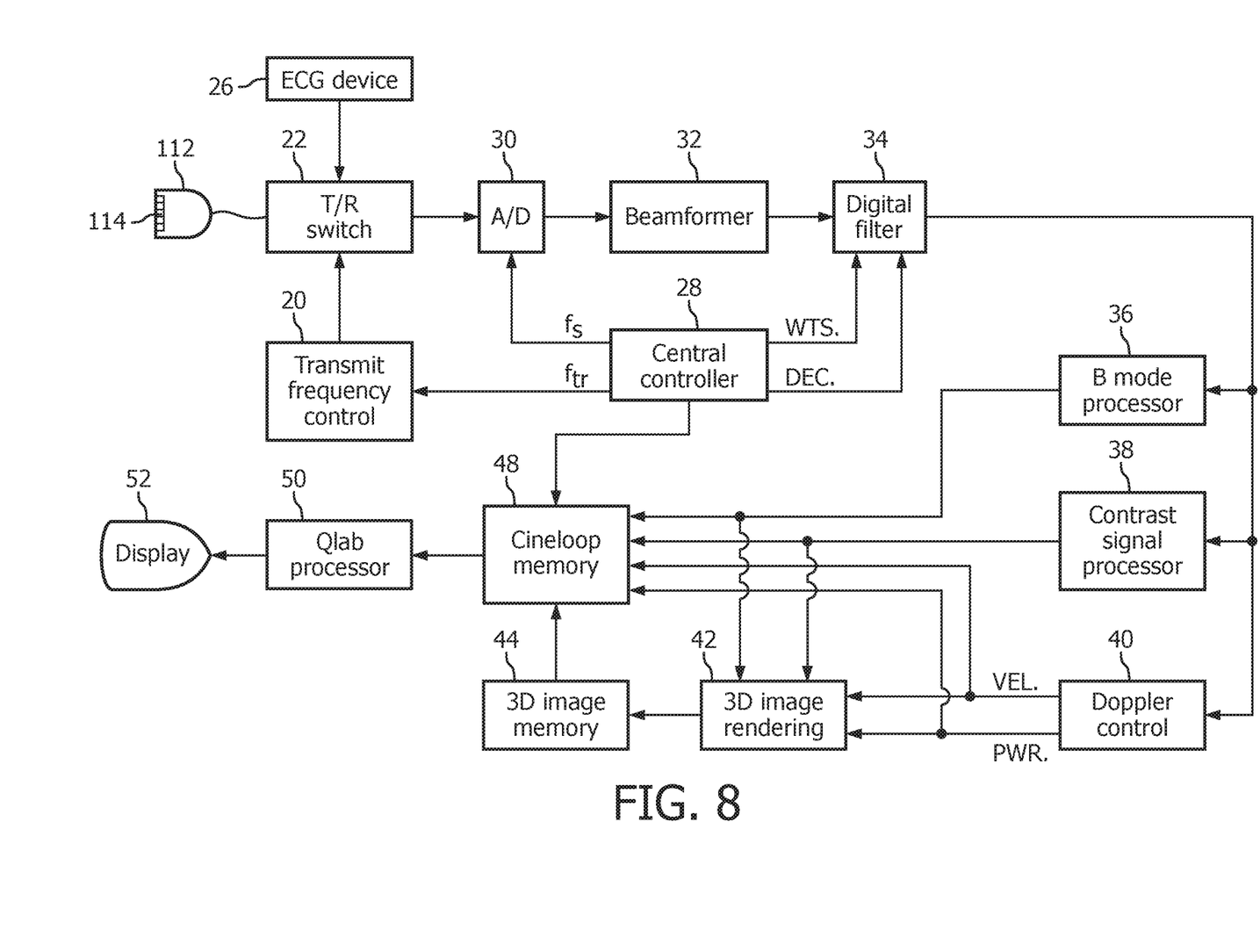
FIG. 8 illustrates in block diagram form an ultrasound system constructed in accordance with the principles of the present invention.

FIG. 8 illustrates an ultrasound system constructed in accordance with the present invention to process cardiac images with curved medial axes and less oval transverse cross-sections as described above. An ultrasonic probe 112 includes an array 114 of ultrasonic transducers that transmit and receive ultrasonic pulses. The array may be a one dimensional linear or curved array for two dimensional imaging, but preferably it is a mechanically swept one-dimensional array or a two dimensional matrix of transducer elements for electronic beam steering in three dimensions. The three dimensional data sets and images described above are preferably acquired using 3D probe with these array types which are capable of acquiring a 3D data set of the heart. The ultrasonic transducers in the array 114 transmit ultrasonic energy and receive echoes returned in response to this transmission. A transmit frequency control circuit 20 controls the transmission of ultrasonic energy at a desired frequency or band of frequencies through a transmit/receive ("T/R") switch 22 coupled to the ultrasonic transducers in the array 114. The times at which the transducer array is activated to transmit signals may be synchronized to an internal system clock (not shown), or may be synchronized to a bodily function such as the heart cycle, for which a heart cycle waveform is provided by an ECG device 26. When the heartbeat is at the desired phase of its cycle as determined by the waveform provided by ECG device 26, such as end diastole or end systole, the probe is commanded to acquire an ultrasonic image dataset. With an electronically steered and focused two dimensional array, the 3D datasets can be acquired as a real time sequence of 3D cardiac datasets. The frequency and bandwidth of the ultrasonic energy generated by the transmit frequency control circuit 20 is controlled by a control signal $f_{tr}$ generated by a central controller 28. Echoes from the transmitted ultrasonic energy are received by the transducers in the array 114, which generate echo signals that are coupled through the T/R switch 22 and digitized by analog to digital ("A/D") converters 30 when the system uses a digital beamformer. Analog beamformers may also be used. The A/D converters 30 sample the received echo signals at a sampling frequency controlled by a signal $f_s$ generated by the central controller 28. The desired sampling rate dictated by sampling theory is at least twice the highest frequency of the received passband, and might be on the order of at least 30-40 MHz. Sampling rates higher than the minimum requirement are also desirable.

The echo signal samples from the individual transducers in the array 114 are delayed and summed by a beamformer 32 to form coherent echo signals. For 3D imaging with a two dimensional array, it is preferable to partition the beamformer between a microbeamformer located in the probe and the main beamformer in the system mainframe as described in U.S. Pat. No. 6,013,032 (Savord) and U.S. Pat. No. 6,375,617 (Fraser), both of which are incorporated herein by reference. The digital coherent echo signals are then filtered by a digital filter 34. The digital filter 34 bandpass filters the signals, and can also shift the frequency band to a lower or baseband frequency range. The digital filter could be a filter of the type disclosed in U.S. Pat. No. 5,833,613, for example, which is incorporated herein by reference. The central controller 28 provides filter weights and decimation control variables for the digital filter 34. Filtered echo signals from tissue are coupled from the digital filter 34 to a B mode processor 36 for conventional B mode processing.

Filtered echo signals of a contrast agent, such as microbubbles, are coupled to a contrast signal processor 38. Contrast agents are often used to more clearly delineate the endocardial wall in relation to contrast agent in the blood pool of the heart chamber, or to perform perfusion studies of the microvasculature of the myocardium as described in U.S. Pat. No. 6,692,438 for example, which is incorporated herein by reference. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950, for instance, which is incorporated herein by reference.

The filtered echo signals from the digital filter 34 are also coupled to a Doppler processor 40 for Doppler processing to produce velocity and power Doppler signals. The output signals from these processors may be displayed as planar images, and are also coupled to a 3D image processor 42 for the rendering of three dimensional images, which are stored in a 3D image memory 44. Three dimensional rendering may be performed as described in U.S. Pat. No. 5,720,291, and in U.S. Pat. Nos. 5,474,073 and 5,485,842, all of which are incorporated herein by reference. Method for generating MPR planes are well known, and include turning data from points in a common plane in a volumetric region of the body into an ultrasonic image of that plane, as described, e.g., in U.S. Pat. No. 6,443,896 (Detmer), which is incorporated by reference herein.

The signals from the contrast signal processor 38, the B mode processor 36 and the Doppler processor 40, and the three dimensional image signals from the 3D image memory 44 are coupled to a Cineloop® memory 48, which stores image data for each of a large number of ultrasonic images. The image data are preferably stored in the Cineloop memory 48 in sets, with each set of image data corresponding to an image obtained at a respective time. The image data in a data set can be used to display a parametric image showing tissue perfusion at a respective time during the heartbeat. The sets of image data stored in the Cineloop memory 48 may also be stored in a permanent memory device such as a disk drive or digital video recorder for later analysis. In this embodiment the image dataset are also coupled to a QLAB processor 50, where the images are processed to produce curved medial axes of the heart chamber and stretched to reduce oval shapes as described above. The QLAB processor can also process curved MPR images to reproduce them in a flat plane as discussed above, and play an animation of the progressive change from a curved plane view to a flat view of the same plane. The QLAB processor also makes quantified measurements of various aspects of the anatomy in the image and delineates tissue boundaries and borders by automated border tracing as described in US patent publication no. US2005/0075567 and PCT publication no. 2005/054898, all of which are incorporated herein by reference. This may be done by fully automated means as described in U.S. Pat. No. 6,491,636, or by assisted automatic border detection as described in the aforementioned US patent publication no. US2005/0075567, all of which are incorporated herein by reference. The data and images produced by the QLAB processor are displayed on a display 52.

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable hardware medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device. Processors can include hardware such as microprocessors, field programmable gate arrays (FPGAs), integrated circuits, or the like.

What is claimed is:

1. An ultrasonic diagnostic imaging system for cardiac diagnosis, comprising:
    an ultrasound probe; and
    a processor configured to:
        acquire, using the probe, three dimensional ultrasound image datasets including a heart;
        produce image data of a myocardium and a heart chamber from the three dimensional ultrasound image datasets;
        delineate a curved medial axis of a long axis view of the heart chamber in the image data between a longitudinally separated apex and valve plane that is more evenly positioned between opposite walls of the myocardium as compared to a straight medial axis between the apex and the valve plane;
        produce a short axis view of a plane intersecting the curved medial axis including editing control points for a border of the myocardium on evenly angularly distributed lines emanating from the delineated curved medial axis in the plane of the short axis view that are more symmetrically distributed around the curved medial axis as compared to their uniform radial distribution about a straight medial axis between the apex and the valve plane; and control a display to display a heart chamber image in a plane defined by the curved medial axis.

2. The ultrasonic diagnostic imaging system of claim 1, wherein the processor is further configured to cause the system to display the long axis heart chamber view in a plane defined by the curved medial axis.

3. The ultrasonic diagnostic imaging system of claim 1, wherein the processor is further configured to cause the system to produce the short axis view normal to the curved medial axis.

4. The ultrasonic diagnostic imaging system of claim 1, wherein the processor is further configured to cause the system to delineate a long axis myocardial border.

5. The ultrasonic diagnostic imaging system of claim 1, wherein the processor is further configured to cause the system to delineate the myocardial border as a short axis myocardial border.

6. The ultrasonic diagnostic imaging system of claim 1, wherein the processor is further configured to cause the system to stretch the myocardium in the image data to produce an image of an adjusted myocardial shape in the short axis view which appears more circular as compared to t+,+'----.:, previous myocardial shape in the image data prior to the stretch.

7. The ultrasonic diagnostic imaging system of claim 1, wherein the processor is further configured to cause the system to produce a first heart chamber image with the curved medial axis and a second heart chamber image with the curved medial axis straightened.

8. The ultrasonic diagnostic imaging system of claim 4, wherein the processor is further configured to cause the system to locate a second plurality of editing control points on the long axis border.

9. The ultrasonic diagnostic imaging system of claim 5, wherein the processor is further configured to cause the system to delineate the editing control points on the lines emanating from the curved medial axis and intersecting the short axis myocardial border.

10. The ultrasonic diagnostic imaging system of claim 7, wherein the processor is further configured to cause the system to produce and display a sequence of heart chamber images over which the curved medial axis changes progressively to a straightened medial axis.

11. The ultrasonic diagnostic imaging system of claim 10, wherein the processor is further configured to cause the system to show the sequence of heart chamber images over which the curved medial axis changes to a straightened medial axis as an animation.

12. A method of diagnosing a patient by ultrasonic cardiac imaging comprising:

acquiring a sequence of three dimensional image datasets of a heart;

extracting a long axis view of a myocardium and heart chamber from the sequence of three dimensional image datasets;

delineating a curved medial axis of the heart chamber between an apex and valve plane which is more evenly spaced between opposite walls of the myocardium than a straight medial axis between the apex and the valve plane;

extracting a short axis view of the myocardium and heart chamber from the sequence of three dimensional image datasets; and displaying editing control points for a border of the myocardium in the short axis view on evenly angularly distributed lines emanating from the delineated curved medial axis in a plane of the short axis view that are more symmetrically distributed around the curved medial axis as compared to their uniform radial distribution about a straight medial axis between the apex and the valve plane.

13. The method of claim 12, further comprising:

extracting the short axis view of the myocardium in a plane substantially orthogonal to the curved medial axis; and locating the editing control points on the border of the myocardium in the short axis view which are on the distributed lines passing through the curved medial axis.

14. The method of claim 13, further comprising:

stretching the myocardium in the short axis view to a shape which appears to have a smoother rounding in comparison to a previous myocardial shape prior to the stretching.

* * * * *